United States Patent
Horst et al.

(10) Patent No.: US 10,975,351 B2
(45) Date of Patent: Apr. 13, 2021

(54) BOS TAURUS VARIETY 'JE840003146074527' AND METHODS OF USE THEROF

(71) Applicant: ABS Global, Inc., DeForest, WI (US)

(72) Inventors: Aaron Horst, Chambersburg, PA (US); Katrina Dattilo, Waunakee, WI (US); Devan Funk, DeForest, WI (US)

(73) Assignee: ABS Global, Inc., DeForest, WI (US)

( * ) Notice: Subject to any disclaimer, the term of this patent is extended or adjusted under 35 U.S.C. 154(b) by 6 days.

(21) Appl. No.: 16/443,418

(22) Filed: Jun. 17, 2019

(65) Prior Publication Data
US 2020/0390089 A1 Dec. 17, 2020

(51) Int. Cl.
| | |
|---|---|
| *C12N 5/071* | (2010.01) |
| *A01N 1/02* | (2006.01) |
| *C12N 5/076* | (2010.01) |
| *A61D 19/02* | (2006.01) |
| *C12N 5/075* | (2010.01) |
| *A01K 67/027* | (2006.01) |

(52) U.S. Cl.
CPC .......... *C12N 5/0602* (2013.01); *A01K 67/027* (2013.01); *A01N 1/0268* (2013.01); *A61D 19/024* (2013.01); *C12N 5/061* (2013.01); *C12N 5/0609* (2013.01); *A01K 2227/101* (2013.01); *C12N 2517/00* (2013.01)

(58) Field of Classification Search
CPC ............ A01K 67/027; A01K 2227/101; C12N 5/0602; C12N 5/061; C12N 5/0609
See application file for complete search history.

(56) References Cited

U.S. PATENT DOCUMENTS

| | | |
|---|---|---|
| 6,011,197 A | 1/2000 | Strelchenko et al. |
| 9,868,962 B2 | 1/2018 | May et al. |
| 2003/0157475 A1 | 8/2003 | Schenk |

FOREIGN PATENT DOCUMENTS

| | | |
|---|---|---|
| WO | WO 2015/148761 | 10/2015 |
| WO | WO 2017/132239 | 8/2017 |

OTHER PUBLICATIONS

Printout from CDCB get cow evaluation. Queries.uscdcb.com. p. 1-1, printed Jan. 13, 2020 (Year: 2020).*
Hinch et al. Science 363, 1300 (2019) pp. 1-10 (Year: 2019).*
Printout from plant variety | InforMEA. https://www.informea.org/en/terms/plant-variety. Printed Jan. 8, 2020. pp. 3 of 3 (Year: 2020).*
Ruiz Rejon. Clones: Identical but Different. Dec. 29, 2014. Printed from https://www.bbvaopenmind.com/en/science/bioscience/clones-different/ pp. 1-5. (Year: 2014).*
Burkard et al., "Precision engineering for PRRSV resistance in pigs: Macrophages from genome edited pigs lacking CD 163 SRCR5 domain are fully resistant to both PRRSV genotypes while maintaining biological function," *PLOS Pathogens* 13(2) (2017).
Park, et al., "Role of stem cells in large animal genetic engineering in the TALENs-CRISPR era," *Reprod Fertil Dev* 26:65-73 (2014).
Park et al., "Generation of germline ablated male pigs by CRISPR/Cas9 editing of the NANOS2 gene," *Scientific Reports* (2017).
Ross et al., "Bovine Somatic Cell Nuclear Transfer," *Methods Mol Biol.* 636. 155-77 (2010).
Whitworth et al., "Use of the CRISPR/Cas9 System to Produce Genetically Engineered Pigs from In Vitro-Derived Oocytes and Embryos," *Biology of Reproduction* 91(3):78 (2014).
Generation Count 3 or GC 4-6 with BBR 93 and Lower: Top Females by Genomic JPITM (GJPI) Dec. 2018 published by the American Jersey Cattle association at https://greenbook.usjersey.com/Portals/2/2018/December/Monthly12to3/1218_Top500.pdf (retrieved Jun. 19, 2019) (See No. 20).
Performance and Progeny Report for JE840003136549962, first available Mar. 7, 2017, retrieved from https://queries.uscdcb.com/CAevalfiles.htm on Jun. 19, 2019.
Performance and Progeny Report for JE840003140305947, first available May 9, 2017, retrieved from https://queries.uscdcb.com/CAevalfiles.htm on Jun. 19, 2019.
Performance and Progeny Report for JE840003146074527, first available Oct. 16, 2018, retrieved from https://queries.uscdcb.com/CAevalfiles.htm on Jun. 19, 2019.
Allen A.R., et al., 2010, Compilation of a panel of informative single nucleotide polymorphisms for bovine identification in the Northern Irish cattle population. BMC Genetics 2010, 11:5.

* cited by examiner

*Primary Examiner* — Marcia S Noble
(74) *Attorney, Agent, or Firm* — Elizabeth A. Epstein; Michael Stimson

(57) ABSTRACT

The disclosure relates to Bovine germplasm of *Bos taurus* variety JE840003146074527. Included in the present disclosure are cells comprising the Bovine variety JE840003146074527. Also provided by the present disclosure are tissue cultures of cells, animals obtained from said cells, and parts thereof, including F1 spermatozoa. The disclosure further provides for methods of breeding, selecting, and using the germplasm to improve existing commercial cattle herds generated from in vitro fertilization methods and progeny cattle obtained from in vitro fertilization and implantation and artificial insemination methods.

30 Claims, No Drawings

BOS TAURUS VARIETY 'JE840003146074527' AND METHODS OF USE THEROF

FIELD

The present disclosure relates to the field of *Bos taurus* breeding. In particular, the present disclosure related to *Bos taurus* variety JE840003146074527 having high multi-trait selection indices and high trait transmissibility.

BACKGROUND

There are numerous steps in the development of any new, desirable *Bos taurus* germplasm. *Bos taurus* breeding begins with the analysis and definition of problems and weaknesses of the current germplasm, the establishment of program goals, and the definition of specific breeding objectives. The next step is selection of germplasm that possesses the traits to meet the program goals. A goal is to combine in a single variety an improved combination of desirable traits from the parental germplasm. See Schefers et al., Animal Frontiers 2(1):1-9 (2012).

During breeding, cattle breeders have a variety of sources when making breeding decisions. In addition to genomic data, a number of agencies and organizations collect and release analysis of population data and indexes. Every three months, the Animal Improvement Programs Laboratory (AIPL) of the United States Department of Agriculture releases the newest USDA-DHIA (Dairy Herd Improvement Association) genetic evaluations for dairy bulls and cows. The AIPL calculates genetic evaluations for type for various breeds, and many breed associations provide their own indexes or other strategies for evaluating certain breed-relevant traits. U.S. dairy genetic evaluations are computed every four months by the Council on Dairy Cattle Breeding (CDCB) and American Jersey Cattle Association (AJCA). Both CDCB and AJCA traits provide the breeder with important comparative data to evaluate the complex genetic and phenotypic traits to develop improved and desirable *Bos taurus* germplasm. For Holstein and Jersey sires, for example, evaluations are genomically enhanced and represent a blending of genomic data, pedigree information, and results from progeny. These genetic evaluations provide the breeder with important information for the selection of desirable germplasm and the development of new and valuable inseminates.

There is a continuous need to develop improved *Bos taurus* germplasm for use in improving production herds as well as for the continued improvement of elite animals.

SUMMARY

The present disclosure provides for and includes elite *Bos taurus* germplasm. In various embodiments of the present teachings can provide for a *Bos taurus* cell of variety Animal, a representative sample of which comprises the Deposit. In some configurations, the *Bos taurus* cell can further comprise a plurality of the cell comprising a frozen vial of the plurality of the cell, a cell culture, a tissue, a zygote, an embryo, a calf, or a mature adult. In various configurations, the *Bos taurus* cell can further comprise a plurality of the cell comprising a cow or heifer. In various configurations, the *Bos taurus* cell can be an oocyte or an ova matured therefrom. In some configurations, the oocyte or ova can be an isolated oocyte or an isolated ova matured therefrom. In some configurations, the oocyte or ova is isolated for in vitro fertilization. In various configurations, the oocyte can be matured into an ovum.

In some embodiments, a *Bos taurus* cell produced by somatic cell nuclear transfer of a genome can comprise *Bos taurus* variety Animal, a representative sample of Animal comprising the Deposit. In some configurations, the *Bos taurus* cell can further comprise a plurality of the cell comprising a frozen vial of the plurality of the cell, a cell culture, a tissue, a zygote, an embryo, a calf, or a mature adult. In various configurations, the *Bos taurus* cell can further comprise a plurality of the cell comprising a cow or heifer. In various configurations, the genome of variety Animal can comprise at least one edited gene.

In some embodiments, the present teachings provide for an include a *Bos taurus* cell from an F1 offspring of an animal of variety Animal, a representative sample of Animal comprising the Deposit. In various configurations, the *Bos taurus* cell from an F1 offspring cell can further comprise a plurality of cells comprising meat. In various configurations, the *Bos taurus* cell from an F1 offspring can further comprise a plurality of the cell comprising a frozen vial of the plurality of the cell, a cell culture, a tissue, a zygote, an embryo, a calf, or a mature adult. In various configurations, the *Bos taurus* cell from an F1 offspring can further comprise a plurality of the cell comprising a bull. In various configurations, the *Bos taurus* cell from an F1 offspring can further comprise a plurality of the cell comprising a cow or heifer. In various configurations, the offspring can be conceived using in vitro fertilization. In various configurations, the offspring can be conceived by artificial insemination of a superovulated cow or heifer. In various configurations, the offspring can be conceived by in vitro fertilization of an ovum obtained from a superovulated cow or heifer. In various configurations, the offspring is gestated by a surrogate animal. In various configurations, the F1 offspring can be a gene edited animal.

In various configurations, the *Bos taurus* cell from an F1 offspring can be a haploid cell. In some configurations, the cell can be a gamete. In some configurations, the cell can be an ovum. In various configurations, the cell can be a sperm. In some configurations, the *Bos taurus* sperm can further comprise a plurality of sperm comprising semen. In some configurations, the semen can be contained in a straw. In some configurations, the semen can be cryopreserved. In various configurations, the haploid cell can comprise at least one edited gene.

DETAILED DESCRIPTION

A goal of a *Bos taurus* breeding program is to combine in a single *Bos taurus* variety an improved combination of desirable traits from the parental germplasm that provides for desirable progeny when used in artificial insemination programs, in vitro fertilization programs, Embryo transfer programs, or a combination thereof. Improved *Bos taurus* inseminate varieties are useful for various artificial breeding techniques, including artificial insemination ("AI") and embryo transfer ("ET"). Improved *Bos taurus* germplasm, varieties, oocytes, embryos, and inseminates prepared therefrom, are desirable.

The present disclosure provides for, and includes, an improved elite germplasm obtained from a multigenerational breeding program. The germplasm is unique and readily distinguishable from germplasm present in non-selected cattle. Indeed, in the absence of continued selection, the germplasm reverts to heterogeneity and diversity. As provided herein, the germplasm of the present disclosure is identifiable using standard methods and the germplasm can be readily identified in progeny generations.

It is to be understood that the disclosure is not necessarily limited in its application to the details set forth in the following description or exemplified by the Examples. The disclosure is capable of other aspects or of being practiced or carried out in various ways.

Definitions

"Animal" as used herein, refers to cells, animals, or particularly gametes and embryos of Bos taurus variety JE840003146074527. The terms "Animal" and "JE840003146074527" are used interchangeably without any change in their meaning.

"Animal Germplasm" as used herein, refers to the germplasm of Animal, or the germplasm of a cell derived from Animal.

"Animal F1 Germplasm" as used herein, refers to the germplasm of Animal's offspring, or the germplasm of a cell derived from Animal's offspring.

"Deposit" as used herein, refers to a representative sample of cells of Animal deposited under ATCC Accession No. PTA-126146 on Sep. 12, 2019 to the American Type Culture Collection, 10801 University Boulevard, Manassas, Va. 20110-2209.

"Sire" as used herein, refers to the sire of Animal, Bos taurus variety JE840003140305947.

"Dam" as used herein, refers to the dam of Animal, Bos taurus variety JE 840003136549962.

"Paternal Grand-Sire" as used herein, refers to the paternal grand sire of Animal, Bos taurus variety JE840003124526334.

"Paternal Grand-Dam" as used herein, refers to the paternal grand dam of Animal, Bos taurus variety JE840003011843660.

"Maternal Grand Sire" as used herein, refers to the maternal grand sire of Animal, Bos taurus variety JE840003124526245.

"Maternal Grand Dam" as used herein, refers to the paternal grand dam of Animal, Bos taurus variety JE840003124526579.

Offspring, as used herein, refers to the progeny of an animal created through natural service, artificial insemination, or in vitro fertilization (IVF).

As used herein, "germplasm" includes intact genomes comprising chromosomes present in cells or nuclei. The term "germplasm" may include any gamete or germ cell, or any somatic cell from which an animal can be cloned.

As used herein the term "about" refers to ±10%.

As used herein, the singular forms "a," "an," and "the" include plural references unless the context clearly dictates otherwise. For example, the term "a compound" or "at least one compound" may include a plurality of compounds, including mixtures thereof.

For the purposes of this disclosure, the term "semen" means seminal fluid which may contain sperm (also referred to as "spermatozoa") secreted by the gonads of a male animal which can be collected from the male animal by any method known to those in the animal breeding arts.

During breeding, to maintain and improve the germplasm, selections of a second parent may be an elite second parent having superior traits. The improved germplasm of the present disclosure can be maintained by selecting superior breeding partners in the F1 and later progeny generations. By suitable selection of the second parent, the germplasm can be maintained. Even further, careful selection of elite breeding partners results in elite progeny.

As used herein, "gamete" refers to a haploid germ cell and includes either a sperm or an ovum and may be used interchangeably. Generally, the identity as a sperm or an ovum can be determined by the context as bulls produce sperm and cows produce ova. For the purposes of this disclosure the term "sperm" means the haploid cell that is the gamete of a male animal which may join an egg (also referred to as "ovum") to produce a zygote and broadly encompasses infertile sperm, sperm having a comparably lesser or a comparably greater fertility between a first amount of sperm obtained from a first animal and a second amount of sperm obtained from a second animal and which may be obtained in the form of a raw ejaculated semen, frozen semen, as sperm separated from the semen and contained in an extender or diluent, or as sex-selected sperm.

As used herein, the term "inseminate" is intended to broadly encompass an amount of sperm whether contained in semen alone or together with cryoprotectant, extender, or other diluent. Inseminates may optionally include one or more "extenders" and diluents which can be utilized to fertilize the eggs of a female animal whether in vitro or in vivo. As used herein, inseminates can further include sex-selected sperm compositions.

As used herein, the term "sex-selected sperm" means sperm which have been separated, regardless as to the method of separation, into subpopulations containing X-chromosome bearing sperm and Y-chromosome bearing sperm having a purity in the range of about 70 percent ("%"), 80%, 90%, and about 100%.

As used herein, the term F1 refers to the first filial generation—progeny born from the gametes of a particular parent. Therefore, as used herein, an F1 Animal is a direct genetic reproduction descendent of Animal.

Phenotypic Traits and Indices

Predicted Transmitting Abilities (PTAs) can be computed for various traits, for example in the broad categories of production (milk and milk components), health/fitness, and type. Dairy cattle are evaluated for the traits of milk, fat, and protein yield, length of productive life, and somatic cell score (an indicator of mastitis). Evaluation procedures combine information from relatives of an evaluated animal, and from the animal itself in the case of cows. Additionally, numerous type or conformation traits are evaluated routinely.

An important aspect of Bos taurus breeding programs are genetic values for yield, management traits, and type that are reported as PTAs. These important traits include higher milk, protein and fat yield PTAs shown as added pounds of milk, fat, and protein expected per lactation for average daughters of individual sires. PTAs are also expressed as percentage traits that are represented as percentage point differences where plus values indicate higher concentration of fat and protein in milk. Bos taurus animals and cells obtained therefrom are also selected to provide increased numbers of daughters and herds contributing to production, improved reliability, improved productive life, improved somatic cell score (SCS). Desirable Bos taurus varieties provide higher daughter pregnancy rates (DPR) that are a genetic measure of the percentage of non-pregnant cows that become pregnant during each 21-day period (heat cycle). Another important and desirable PTA selected by breeders is the productive life (PL) that is the additional months of life in the milking string. Also included among the desirable PTAs are calving related traits such as the service sire calving ease and the service sire stillbirth.

Traits are typically combined into an index based on their relative economic weights. For example, the Net Merit index (NM$) computed by USDA AIPL in conjunction with CDCB estimates lifetime profit based on incomes and expenses relevant for today's dairy producers and is expressed as a dollar value. Traits included in NM$ are: protein (lb.), fat (lb.), productive life, somatic cell score, udder composite, feet/legs composite, body size composite and daughter pregnancy rate. Calving ability also is included in NM$ calculations for Holsteins and Brown Swiss. The traits incorporated into calving ability for Holsteins are daughter stillbirth, service sire stillbirth, daughter calving ease, and service sire calving ease. Only the two calving ease traits are available for inclusion in calving ability values of Brown Swiss. Net merit scores are a relative score calculated based on a comparison with a baseline average animal in 2010. A new baseline animal based on the average animal in 2015 is expected to begin use in 2020 and will reflect improvements to dairy herds generally. Under the new NM$, it is anticipated that NM$ scores in 2020 will be reduced by about 150 to 200 points compared to earlier NM$ scores. As used herein, NM$ scores are calculated using the 2010 baseline and persons of ordinary skill in the art will be able to calculate or convert NM$ values based on the 2010 baseline population and 2015 baseline population. Methods to calculate NM$ are known in the art. See VanRaden et al., "Net merit as a measure of lifetime profit: 2018 revision," USDA AIP Research Report NM$7 (5-18) (2018) available at aipl(dot)arsusda(dot)gov/reference/nmcalc-2018.htm for exemplary purposes only (this recent publication uses updated baseline animals not yet in use by the industry for Net Merit calculations.) The NM$ incorporates production, management and important composite traits and is designed for dairies paid for protein plus fat and requiring more emphasis on management traits. The present disclosure provides for, and includes, increased NM$ of progeny cattle relative to parents. In an aspect, the NM$ of progeny cattle is increased by at least 10% over the parent generation. Also included are methods to improve NM$ in a herd comprising crossing an Animal of the present disclosure with individuals of a herd in need of improvement.

Trait parameters have been correlated with the underlying genetics and the heritabilities determined. The genetic and phenotypic correlations among the twelve PTA traits are also provided by VanRaden et al., 2018.

The JERSEY PERFORMANCE INDEX™ (JPI™, American Jersey Cattle Association, Reynoldsburg, Ohio), which is used by the American Jersey Cattle Association, is comprised of the following traits: protein, fat, functional trait index, productive life, somatic cell score, and daughter pregnancy rate. This functional trait index is based on the bull/cow PTAs for all type traits. The JPI™ is updated periodically in the interest of improving the breed. Values provided herein are calculated using the formula released in 2017. Information about this index can be found on usjersey (dot)com. Persons skilled in the art will be able to convert between indexes as new versions are released.

Using a selection index can be an effective way to consider several traits when choosing breeding stock. Conventional animal husbandry strategies often rely on selection indexes, particularly for choosing service sires.

Breeding stock sires and sire lines are typically chosen based upon their size and fertility. Prior successes in mating as well as siring females are both traits that are often utilized in selecting sires and/or sire lines.

Also, knowing where service sires rank relative to other active bulls is typically considered to be helpful in determining if the sires meet a particular herd's genetic goals. Selection indexes can be particularly useful in monitoring such ranking. To maximize genetic improvement using a selection index, it is usually recommended that the service sires for a given herd average at or above the 80th percentile.

In germplasm improvement programs, "Dams of Males" (DM) or more commonly, "bull mothers" represent a group of elite females that are selected based on estimated breeding values (EBV) or genomic breeding values (GEBV) and that usually rank among the top 1% of the population. These elite females are typically mated to elite bulls from the "Sires of Males" (SM) group for the purpose of producing elite bull calves.

"Sires of males" (SM) or "sires of sons" are elite males that are also selected by EMT or GEBV to be sires of the next generation of young elite bulls and represent <5% of the males. It is the SM semen that is marketed to dairy farmers and it is primarily through the distribution of SM semen that commercial herds are improved.

Sires of females (SF) or "active AI sires" represent a larger group of males that have been selected based on EBV or GEBV and whose semen is used to breed the general population and produce replacement females for commercial farms.

"Dams of Females" (DF) or "commercial cows" represent the large population of females that are primarily used to produce milk rather than breeding stock and are routinely mated to bulls from the "Sires of Females" (SF) group to initiate lactation, resulting in the next generation of replacement heifers.

Germplasm development programs are directed to the continued improvement of the elite (DM and SM) individuals that in turn improve the germplasm of the larger DF and SF populations. Distinct DM and SM lines have been developed to serve different markets and the resulting germplasms are distinct. That is, different DM and SM lines have distinctive sets of alleles as a result of multigenerational selections.

Ranchers and dairy farmers increase the value of a cow's calves by utilizing frozen semen from the most valuable SM bulls in the industry to breed their cows. Frozen semen can be shipped commercially around the world, the best bulls can be mated to thousands of cows instead of the usual 20 to 40 under natural pasture mating conditions. Once thawed, the semen can be used as an inseminate.

As used herein, daughter pregnancy rate (DPR) is a genetic measure of the percentage of non-pregnant cows or heifers eligible to become pregnant that actually become pregnant during each 21-day period (heat cycle). DPR is similar to, but not always the same as, pregnancy rates computed for herd management purposes. Daughters of sires which have larger PTA DPR are more likely to conceive during a given heat cycle and each 1% increase in PTA DPR is associated with a genetic decrease of 4 days open.

As used herein, Cow Livability (LIV) represents the probability value of a lactation not ending in death or euthanasia relative to the average of the breed. This trait is important because cows that die during lactation have no value and the farmer must pay to dispose of the carcass. The trait similar to PL which includes cows culled from the herd for any reason. LIV values range from about −5 to +5, where 5% more of a bull's daughters will remain alive compared to the breed average.

As used herein, heifer conception rate (HCR) is the percentage of inseminated heifers that become pregnant at each service, shown as a deviation in percentage.

As used herein, cow conception rate (CCR) is the percentage of inseminated cows that become pregnant at each service, shown as a deviation in percentage.

As used herein, estimated future inbreeding (EFI) is the estimate of future progeny inbreeding, assuming that an animal is mated randomly within their given breed.

As used herein, kappa casein (K-casein) identify sires with homozygous BB genotype for Kappa Casein for preferred cheese production.

As used herein, predicted transmitting ability protein (PTAP) is a yield trait for protein measured in pounds that is the predicted difference of the protein yield of the offspring from the average. PTAP is shown as added pound of protein expected per lactation for average daughters of individual sires. Higher numbers are preferred.

As used herein, predicted transmitting ability fat (PTAF) is a yield trait for fat measured in pounds that is the predicted difference of the fat yield of the offspring from the average. PTAF is shown as added pound of fat expected per lactation for average daughters of individual sires. Higher numbers are preferred.

As used herein, predicted transmitting ability milk (MILK or PTA MILK) is a yield trait for milk measured in pounds that is the predicted difference of the milk yield of the offspring from the average. MILK is shown as added pounds of milk expected per lactation for average daughters of individual sires. Higher numbers are preferred.

As used herein, feed efficiency value (FE) recognizes cattle with the ability to produce large volumes of milk without having to consume a great deal of feed, based on the following formula: Feed Efficiency=(Dollar value of milk produced)−(Feed costs for extra milk)−(Extra maintenance costs).

As used herein, predicted transmitting ability type (PTAT or TYPE) is represented as differences in points from a base population physical conformation. Daughter final scores are collected by breed classifiers. Raw scores then are adjusted for cow age and used to derive Type PTAs (PTAT). These PTAT are represented as differences in points from the base population. TYPE values are normalized to enable comparisons across different base populations through time. Higher numbers correlate with more desirable physical conformations.

As used herein, STA dairy form (DF or DFM), formerly known as "dairy character", refers to sharpness, angularity, flatness of bone, openness of rib and length of neck that provides an indication of 'milkiness' and reflects the ability of a dairy cow to produce milk from the feed over flesh and fat.

Dairy cattle are evaluated and described using criteria generally known as linear descriptive traits that are well known in the art. These linear descriptive traits include Stature (STA), Strength (STR), Body Depth (BDE), Rump Angle (RPA), Thurl Position, Rump Width, Fore Udder Height (FTA), Fore Udder Attachment (FUA), Rear Udder Height (RUH), Rear Udder Width (RUW), Udder Cleft (UCL), Udder Depth (UDP), Front Teat Placement (FTP), Rear Teat Placement (RTP), Teat Length (TLG), Udder Tilt (UT), Rear Legs (Side View) (RLS), Rear Legs (Rear View) (RLR), Feet Leg Score (FLS), Foot Angle, Thurl Width (TRW), and Body Condition. These linear trait criteria are well known to those skilled in the art. See for example, The Dairy Cow Today: U.S. Trends, Breeding, and Progress Since 1980, S. L. Spahr and G. W. Oppennan, Chapter 9, Type and classification and trait appraisal, hereby incorporated by reference in its entirety.

Linear descriptive traits are often combined into composite indexes to simplify the process of describing the transmitting pattern for type traits. Composite indexes include the feet & legs composite (FLC), the udder composite index (UDC), the body form (BF) composite index, body size composite (BSC) index, and the dairy capacity (DC) composite index. The FLC composite is a combination of rear legs, side view and foot angle linear traits. The UDC incorporates the udder attachment, rear udder height, rear udder width, udder depth, udder cleft, front teat placement, and rear teat placement linear traits. The UDC is designed so that the association between UDC and herd life is maximized. Larger values are associated with longer herd life. The udder composite index describes a well formed capacious udder with strong attachment. Using breeding animals with a high UDC results in a lowering of the somatic cell score and daughters whose udders are trouble-free and capable of holding more milk. The BF index combines the linear traits of stature, body depth, rump angle, and rump width. The DC composite combines the linear traits of dairy form and strength. The BSC is another composite index calculated from four linear traits: stature, strength, body depth and rump width. Every 1.0 STA increase in the BSC correlates with a 24 pound predicted increase in mature body weight.

As used herein, "Productive Life" (PL) is a measure of how long dairy cows survive in a herd after they calve for the first time. It is based on calving dates, culling or death dates, and days in milk (based on dry dates) in each lactation for cows on DHI test. The PTA for Productive Life (PL) is expressed as additional months of life in the milking string. Bulls with larger PL are expected to sire daughters that have longer productive lives. Data used to compute PL include actual longevity, stage of lactation, and culling data supplemented with data from traits that are correlated with PL. By assigning the largest PL credits for months in peak production and by giving later lactations slightly more credit than first lactation, PL reflects the economic impact of cow longevity. The heritability of PL is low at 0.085 and the trait is expressed late in the life of dairy cow. Accordingly, PL is a difficult trait to improve through selection because of low heritability and expression of the trait late in life. Methods for calculating PL are known in the art. See VanRaden et al., *Journal of Dairy Science* 76:2758-2764 (1993), VanRaden et al., *Journal of Dairy Science* 78:631-638 (1995), Weigel et al., *Journal of Dairy Science* 81:2040-2044 (1998). Each of the foregoing references are hereby incorporated by reference in their entireties. See also VanRaden et al., "Methods used to compute multi-trait productive life," USDA AIPL Research Report PLC (11-03) available at aipi(dot)arsusda(dot)gov/reference/multi-pl.htm. The present disclosure provides for, and includes, progeny cattle having an increased PL relative to a dam parent.

As used herein, "Somatic Cell Score" (SCS) is calculated from the Somatic Cell Count (SCC). When milk is produced, a small number of cells are also transferred to the milk (along with the proteins, fat, water, and minerals that make up milk.) Although all milk contains some of these cells, milk quality is affected if they are present in very high numbers. Milk processors limit the concentration of cells that they will allow in milk they buy from farmers. Also, knowing the SCS for an individual cow can help the farmer tell if the cow is healthy because irritation in the udder can cause higher SCS. Health management has the biggest effect on SCS, but just like some people inherit a higher chance of getting ear infections, cows can inherit traits which cause higher SCS. Next to traits like milk or protein production, SCS has a low heritability. Somatic Cell Score PTA is calculated using somatic cell score data from the first five lactations as an indicator of mastitis resistance. Bovines with the lowest PTA SCS are expected to have daughters with the lowest SCS, the lowest somatic cell counts (SCC), and the fewest cases of mastitis. The present disclosure provides for, and includes, reduced SCS in progeny compared to a dam parent.

As used herein, "Fertility Index" (FI) combines several reproductive components into one overall index: ability to conceive as a heifer, ability to conceive as a lactating cow, and a cow's overall ability to start cycling again, show heat, conceive, and maintain a pregnancy. The Fertility Index is derived from the formula: Fertility Index=18% Heifer Conception Rate (HCR)+18% Cow Conception Rate (CCR)+ 64% Daughter Pregnancy Rate (DPR). The present disclosure provides for, and includes, an increased FI in progeny compared to a dam parent. Also included are methods to improve FI in an offspring comprising crossing an Animal of the present disclosure with bulls of a herd in need of improvement.

Breeders have developed merit measures for the evaluation of value of improved *Bos taurus* germplasm over the lifetime of offspring. Various merit measures account for the additional net profit that an offspring of an animal will provide over its lifetime. Income and expenses for a typical dairy operation have been estimated, so that a measure of overall net profit can be calculated. Three different values (Net, Fluid and Cheese) of lifetime profitability are available. The primary difference between the formulas is the emphasis that is placed on the components. When breeding, producers select the index that is closest to the milk payment in their area. Net merit is based upon the future anticipated average milk price for all of the United States. Fluid Merit would be for producers who do not receive any payment for protein. In the Fluid Merit formula, a negative value is placed on protein because additional feed is required to produce additional protein. Without a direct payment for the additional protein, this results in a negative value. Cheese Merit may be appropriate for farmers selling their milk directly to a cheese plant.

As used herein, grazing merit (GM$) is an index that incorporates economic values appropriate for grazing production in the U.S. The GM$ index is based upon appropriate costs and revenues to allow for selection of cows and bulls for more optimal genetic progress. GM$ is geared toward herds on pasture systems, with those breeders often demanding higher fertility, compared to conventional systems, due to seasonal calving requirements. Methods to calculate GM$ are known in the art. See Gay et al., J. Dairy Sci. 97:4568-4578 (2014), hereby incorporated by reference in its entirety. The present disclosure provides for, and includes, increased GM$ of progeny cattle relative to parents. In an aspect, the GM$ of progeny cattle is increased by at least 10% over the parent generation. Also included are methods to improve GM$ in a herd comprising crossing an Animal of the present disclosure with individuals of a herd in need of improvement.

As used herein cheese merit (CM$) is an index that incorporates economic values appropriate for milk sold to be made into cheese or other dairy products. The formula incorporates MILK, PTAF, PTAP, and various health and type traits. A discussion of CM$ is available on us(dot)altagenetics(dot)com. The present disclosure provides for, and includes, increased CM$ of progeny cattle relative to parents. In an aspect, the CM$ of progeny cattle is increased by at least 10% over the parent generation. Also included are methods to improve CM$ in a herd comprising crossing an Animal of the present disclosure with dams of a herd in need of improvement.

As used herein, fluid merit (FM$) is an index that incorporates economic values for dairy production wherein the producers do not receive any payment for protein. Methods for calculating FM$ are known in the art. The present disclosure provides for, and includes, increased FM$ of progeny cattle relative to parents. In an aspect, the FM$ of progeny cattle is increased by at least 10% over the parent generation. Also included are methods to improve FM$ in a herd comprising crossing an Animal of the present disclosure with individuals of a herd in need of improvement.

As used herein, a haplotype is a combination of alleles (DNA sequences) at different locations on a chromosome that are transmitted together as a group (linked). Haplotype tests are available that provide for the identification of recessive disorders that affect fertility and other traits. See Cole et al., "Haplotype tests for recessive disorders that affect fertility and other traits," USDA AIP Research Report Genomic3 (09-13) updated Dec. 1, 2018, available at aipl(dot)arsusda(dot)gov/reference/recessive_haplotypes_ARR-G3.html. Certain haplotypes are undesirable in a *Bos taurus* germplasm as provided in the present specification. When the recessive haplotype is homozygous, fertility and other critical traits are significantly affected. The germplasm of the present disclosure can be used to improve herds and reduce the presence of these undesirable haplotypes.

Undesirable recessive haplotype mutations include polledness (lack of horns—which is considered bad for animal welfare—haplotype JHP). Several haplotypes do not produce viable homozygous offspring, including JH1 and JH2 in Jersey cattle. JH1 is a imitation in CWC15. The genetic defect associated with JH2 is still unknown.

Cattle suffer from a number of genetic diseases that are monogenic disorders inherited in a Mendelian fashion. Various genetic diseases are known in the art. See for example, Garrick and Ruvinsky, "The Genetics of Cattle." $2^{nd}$ Edition, CAB International, Oxfordshire UK 2015; see also Parkinson et al., "Diseases of Cattle in Australasia," ISBN 9780958363447 Jolly et al., "Genetic Diseases of Cattle," Chapter 21, each hereby incorporated by reference in their entireties, and vetbook(dot) org/wiki/cow/index.php/Genetic_diseases_of_cows. The germplasm of the present disclosure can be used to reduce the presence of these recessive genes in herds and bovine populations.

Also included and provided for, are *Bos taurus* oocytes or ova matured therefrom derived or isolated from Animal. In some aspects, the mature ova are treated with sperm from an elite bull. In some aspects, the oocytes can be cryopreserved.

Also included and provided for are F1 embryos that are the product of crossing Animal with an elite bull. These embryos can be created by in vitro fertilization or by superovulating Animal and then performing natural service or artificial insemination.

Also included, and provided for, are *Bos taurus* cells that are haploid. Animal Haploid Genotype provides for, and includes, a haploid *Bos taurus* cell or a plurality of haploid *Bos taurus* cells comprising improved germplasm. As described below, haploid cells can be readily produced by somatic cell nuclear transfer of *Bos taurus* variety Animal, wherein a sample of cells of said variety comprises the Deposit. Mature animals prepared from variety Animal can be used to obtain haploid gametes through methods known in the art and discussed in detail below. As used herein, the term "gametes," "sperm," "spermatozoa," "spermatid," and "inseminate" are used interchangeably for haploid cells obtained from male animals and the terms will be understood by a person of ordinary skill in the art. As used herein, the term "gametes," "ova," and "ovum" are used interchangeably for haploid cells obtained from female animals. In an aspect, the number of haploid cells from male animals in a plurality of cells of the present disclosure is two or more, 100 or more, 1000 or more, $10^4$ or more, $10^5$ or more, or $10^6$ or more. In an aspect, the cells are in a container and comprise between $10^4$ and $10^7$ cells. In an aspect, the number of cells in a container is between $10^5$ and $10^7$ cells.

As provided herein, the plurality of haploid cells may be cells in fresh semen. Methods for the collection of sperm from mature bulls are well known in the art.

*Bos taurus* germplasms are often provided as frozen (cryopreserved) semen samples. A long-term semen storage system is advantageous by allowing movement of artificial insemination (AI) doses throughout the world without compromising semen viability. Long-term storage also enables specific health checks to be carried out on both the semen and individual males thus minimizing the risk of the spread of disease through AI. Cryopreservation techniques for semen are well known to those skilled in the art.

As provided herein, useful cryoprotectants are not limited to those acting by a particular mechanism. In an aspect, the cryoprotectant acts, at least in part, by reducing intracellular dehydration. Not to be limited by theory, freezing is accompanied by an increase in solute concentration in the medium surrounding sperm that draws water out of the cells leading to increases in intracellular electrolyte concentration. Cryoprotectants of the present disclosure include, but are not limited to glycerol (GLY), 1,1,1-tris(hydroxymethyl)ethane [2-hydroxymethyl-2-methyl-propane-1,3-diol] (THE), 1,1,1-tris(hydroxymethyl)propane [2-ethyl-2-hydroxymethyl-propane-1,3-diol] (THP), ethylene glycol (EG), propane-1,2-diol (PD2), propane-1,3-diol (PD3) and dimethylsulphoxide (DMSO), sucrose, trehalose, dextrose, raffinose, lactose, melibiose, melezitose, mannotriose, stachyose, dextran, hydroxy-ethyl starch, maltitol, lactitol, polyethyleneglycol, propylene glycol, polyvinyl pyrrolidone, polyethylene oxide, and combinations thereof.

The present disclosure provides for, and includes, containers of *Bos taurus* inseminates comprising a plurality of sperm cells. Inseminates are prepared by combining fresh semen samples with a cryoprotectant and freezing the samples. Upon thawing, the sperm retain high levels of motility and fertility. In addition to the cryoprotectant, inseminates often include one or more additional components. In an aspect, the inseminate comprises $10^4$ or more, $10^5$ or more, or $10^6$ or more cells. In an aspect, the inseminate is provided in a container and comprises between $10^4$ and $10^7$ cells. In an aspect, the number of cells in the container is between $10^5$ and $10^7$ cells.

In general, about 5 ml to about 15 ml of semen is collected from a bull and optionally mixed with a suitable extender and cryoprotectant. For example, in an aspect, about 10 ml of semen is collected and mixed with about 240 ml of TRILADYL™ (Minitube, Verona, Wis.) solution, which is an off the shelf product that is available from Minitube of America in Verona, Wis. The TRILADYL™ contains an extender and a cryoprotectant, such as glycerol. The mixture of semen, extender and cryoprotectant is then placed in plastic straws and frozen. In the industry the contents of the frozen straw are generally referred to as frozen semen, although the contents also contain an extender and a cryoprotectant. A goal is to cryopreserve about 20 million motile sperm in a ½ ml semen straw.

As used herein, an inseminate refers to a composition of *Bos taurus* sperm having an Animal F1 Germplasm and a cryoprotectant. Also provided are inseminates further comprising a component selected from the group consisting of an extender, an antibiotic, a buffer, an energy source, an antioxidant, a protein source, and a combination thereof. Inseminates according to the present disclosure may be frozen or thawed.

The present disclosure further provides for, and includes, *Bos taurus* inseminates comprising a sperm having a genome comprising an Animal Haploid Genotype, the inseminate further comprising one or more extenders. The term "extender" refers to any medium that preserves sperm viability. The term "extension" refers to the dilution of sperm and cryoprotectant (e.g., an inseminate) with extender. An extender suitable for use in the selected sperm sample includes a physiologically acceptable carrier. The physiologically acceptable carrier is typically aqueous, and, in certain aspects, includes deionized water. Suitable extenders commonly comprise one or more of the following additional components: a component that maintains osmolality and buffers pH, an organic substance that prevents cold shock and preserves fertility of sperm, a detergent that acts synergistically with certain organic substances to enhance preservation of sperm, an energy source that can be readily utilized by sperm, an antioxidant, which protects sperm from cold shock, a substance that facilitates sperm capacitation, and one or more antibiotics. In aspects according to the present disclosure, the extender may be a commercial extender, such as BOVIPRO® CRYOGUARD® (MOFA Global, Wis., USA), ANDROMED® (Minitube, Verona, Wis.), ANDROMED® CSS (Minitube, Verona, Wis.), TRILADYL® (Minitube, Verona, Wis.), BILADYL® (Minitube, Verona. Wis.), STERIDYL® (Minitube, Verona, Wis.), and BIOCIPFIOS (IMV, France). See for example U.S. Patent Publication No. 2003/0157475 published Aug. 21, 2003.

The present disclosure further provides for, and includes, *Bos taurus* inseminates comprising at least one sperm derived from a diploid cell comprising Animal F1 Germplasm and further comprising extenders that are a source of protein. Suitable protein sources include, but are not limited to egg yolk, milk, BSA, and derivatives and combinations thereof. Inseminates comprising a protein source may further include one or more additional components selected from the group consisting of osmolytes, a buffer, and organic substances that prevent cold shock, detergents, energy sources, antioxidants, one or more antibiotics, and a combination thereof.

The present disclosure further provides for, and includes, *Bos taurus* inseminates comprising a sperm having a genome comprising a an Animal F1 Germplasm wherein the osmolality of the inseminate is controlled. The term "osmolality," as used herein, is a measure of the osmotic pressure of dissolved solute particles in an aqueous solution (e.g., an extender). The solute particles include both ions and non-ionized molecules. Osmolality is expressed as the concentration of osmotically active particles (i.e., osmoles) dissolved in 1 kg of water.

Substances helpful in maintaining osmolality and pH within these ranges are well known in the art and can be added to the extender as a solid or already in solution. A buffer containing a salt, a carbohydrate, or a combination thereof can be employed for this purpose. In aspects according to the present disclosure, the osmolality is between about 250 milliosmoles (mOsM) to about 350 mOsM. In certain aspects, the pH of the *Bos taurus* inseminate is between 6.9 and 7.5. Specific examples of osmolytes and buffers include sodium citrate, Tris[hydroxymethyl]aminomethane, and TES (N-Tris [Hydroxymethyl]methyl-2-aminoethanesulfonic acid), and monosodium glutamate buffers; milk; HEPES-buffered medium; and any combination thereof. The component employed to help maintain osmolality and provide buffering capacity in a particular application can vary depending on the other components of the extender and, in some cases, on the species from which the sperm are derived. The selection of such a component for use in the present teachings is, however, within the level of skill in the art. Inseminates comprising an osmolyte may further include one or more additional components selected from the group consisting of a protein source, a buffer, and organic substances that prevent cold shock, detergents, energy sources, antioxidants, and one or more antibiotics.

The present disclosure further provides for, and includes, *Bos taurus* inseminates comprising a sperm comprising an Animal F1 Germplasm; wherein the inseminate further comprises extenders that comprise an antibiotic, since substantial bacterial growth can threaten sperm viability and increase the risk of infection of the host in artificial insemination or in vitro fertilization procedures. Any of a variety of antibiotics useful in the cryopreservation of cells can also be employed in the extender. The selection of a suitable antibiotic depends on the species from which the sperm was obtained, the procedures involved in obtaining and handling the sperm sample, and the specific microorganism(s) to be targeted. Exemplary antibiotics include tylosin, gentamicin, lincomycin, spectinomycin, linco-spectin (a combination of lincomycin and spectinomycin), penicillin, streptomycin, and ticarcillin, which can be used alone or in combination. However, one skilled in the art can readily determine other antibiotics suitable for use in the extender. Inseminates comprising an osmolyte may further include one or more additional components selected from the group consisting of a protein source, a buffer, and organic substances that prevent cold shock, detergents, energy sources, antioxidants, and osmolytes.

The present disclosure provides for and includes *Bos taurus* inseminates comprising a sperm comprising an Animal F1 Germplasm; wherein the inseminate further comprises organic stress reducing agents. Organic stress reducing agents (OSR) provide improved motility, viability, fertility, and integrity of sperm cells in the *Bos taurus* inseminates of the present disclosure. Suitable OSRs include, but are not limited to catalase, superoxide dismutase (SOD), a SOD mimic, glutathione, glutathione reductase, glutathione peroxidase, pyruvate, mercaptoethanol, butylated hydroxytoluene (BHT), lipoic acid, flavins, quinines, vitamin K (and related vitamers), vitamin B12 (and related vitamers), vitamin E (and related vitamers), tocopherols, tocotrienols, α-tocopheryl, alpha ketoglutarate (AKG), malondialdehyde (MDA), asymmetric dimethylarginine (ADMA) and biologically active derivatives thereof *Bos taurus* inseminates and compositions according to the present disclosure can include one or more OSRs. Inseminates comprising a one or more OSRs may further include one or more additional components selected from the group consisting of a protein source, a buffer, and organic substances that prevent cold shock, detergents, energy sources, antioxidants, and osmolytes.

The present specification provides for, and includes, inseminates comprising a sperm comprising an Animal F1 Germplasm. In an aspect, the inseminate comprises sperm cells from an offspring of *Bos taurus* variety Animal, wherein a sample of cells of Animal comprises the Deposit. As provided herein, the inseminate may be fresh, frozen, or frozen and thawed and may further comprise a component selected from the group consisting of an extender, an antibiotic, a buffer, an energy source, an antioxidant, a protein source, and a combination thereof.

The present specification provides for, and includes, inseminates wherein the sperm have undergone one or more selections to prepare selected sperm inseminate. In some aspects, selected sperm inseminates may be selected based on sex-type. In some aspects, the sperm are sex selected prior to preparing the selected sperm inseminate. In various aspects, the inseminate is prepared and then subjected to a sex-type selection processes. In various aspects, the sex-type selection is performed prior to freezing the inseminate. In various aspects, the sex-type selection process is performed after thawing of a frozen inseminate.

Sex-type selection may be performed based on slight differences in the physical characteristics of sperm cells. Selection may also be performed based on nucleic acid sequence. A variety of methods are available for selecting cells including flow-cytometric methods. Importantly, the selection and subsequent processing of sperm creates challenges to maintain fertility and successful insemination when used in breeding. Methods of sex-type selection are known in the art.

The present disclosure provides for, and includes, sex selected inseminates comprising sperm having a genome comprising an Animal F1 Germplasm.

In an aspect, the sex selected inseminate comprises sperm cells from an F1 offspring of *Bos taurus* variety Animal, wherein a sample of cells of Animal comprise the Deposit. As provided herein, the sex selected inseminate may be fresh, frozen, or frozen and thawed and may further comprise one or more components selected from the group consisting of an extender, an antibiotic, a buffer, an energy source, an antioxidant, and a protein source. As provided herein, the sex selected inseminate may be skewed toward X-chromosome bearing or Y-chromosome bearing populations of spermatozoa. In an aspect, the sex selected inseminate comprises $10^4$ or more, $10^5$ or more, or $10^6$ or more cells. In an aspect, the sex selected inseminate is provided in a container and comprises between $10^4$ and $10^7$ cells. In an aspect, the number of sex selected cells in the container is between $10^5$ and $10^7$ cells.

The present disclosure provides for, and includes, a container of a *Bos taurus* inseminate comprising a plurality of sperm cells having attributes of an F1 offspring of *Bos taurus* semen variety Animal, wherein a sample of cells of said variety comprise the Deposit.

The present disclosure provides for, and includes oocytes extracted from a cow or heifer comprising an Animal germplasm. The present disclosure further provides for treating the oocytes with TCM-99 (Sreenivas, D. et al., 2013, J. Aller. Ther., 4(2)), or other oocyte maturation media known in the art. TC 199 stock solution is commercially available form Minitube (Verona, Wis.), and other vendors. The present disclosure further provides for and includes methods of capacitation of sperm known in the art (see, for example, Parrish, J J., 2014, Theriogenology., 81(1), 67-73). The present disclosure further provides for and includes methods of in vitro fertilization known in the art for fertilizing mature ova of Animal or her F1 offspring.

The present disclosure provides for and includes methods of Embryo Transfer to increase the number of possible offspring for Animal. The present disclosure provides for and includes superovulation of Animal or her F1 daughters As described in Example 6. The present disclosure further provides for the released ova being fertilized by either artificial insemination or natural service.

The present disclosure provides for, and includes, the distinguishing attributes of Animal and the inseminates of the present disclosure in Table 1. The unexpected and desirable combination of attributes is particularly valuable for dairy herd improvement and breeding purposes. In the following tables, "T" means that the animal tested free of the associated genotype.

TABLE 1

Composite scores, linear trait scores and genomic results for Animal

|  |  |  |
|---|---|---|
|  | Sex | F |
|  | id17 | JE840003146074527 |
|  | Birth Date | 2018 Jul. 20 |
| Net Merit Score | NM$ | 660 |
| productive life | PL | 4.3 |
| somatic cell score | SCS | 2.78 |
| Daughter Pregnancy Rate | DPR | −1.3 |
| Cow Livability | LIV | 0.1 |
| PTA MILK | Milk | 1702 |
| PTAF | Fat | 83 |
| PTAP | Pro | 67 |
| Heifer Conception Rate | HCR | 0.0 |
| Cow Conception Rate | CCR | −0.8 |
| Stature | STA | 0.3 |
| Strength | STR | 0.1 |
| Dairy Form | DFM | 0.5 |
| Rump Angle | RPA | 0.0 |
| Thurl Width | TRW | 0.0 |
| Rear Legs Side View | RLS | 0.2 |
| Fore Udder Height | FTA | 0.2 |
| PTA Type | PTAT | 0.8 |
| Fore Udder Attachment | FUA | 0.3 |
| Rear Udder Height | RUH | 0.3 |
| Rear Udder Width | RUW | 0.4 |
| Udder Cleft | UCL | 0.4 |
| Udder Depth | UDP | 0.8 |
| Front Teat Placement | FTP | 0.0 |
| Teat Length | TLG | 0.3 |
| Udder Composite Index | UDC | 6.4 |
| Cheese Merit Index | CM$ | 690 |
| Jersey Performance Index ™ | JPI ™ | 202 |
| Homozygous lethal haplotype | JH1 | T |
| Homozygous lethal haplotype | JH2 | T |
|  | Dam ID | JE840003136549962 |
|  | Sire ID | JE840003140305947 |
| Maternal Grand Sire | MGS ID | JE840003124526245 |

Also provided for, and included in, the present disclosure, are F1 progeny animals that have desirable EBV or GEBV scores. Such animals are important Sires of Females (SF) that are useful for breeding commercial herds and populations. Like breeding F1 progeny for the production of DM and SM animals, the second parent can be a select parent or an elite parent. Select parents for the production of F1 progeny animals that are either SF or DF animals have positive EBV scores for one or more PTA traits selected from the group consisting of productive life (PL), somatic cell score (SCS), Daughter Pregnancy Rate (DPR), PTA MILK (Milk), PTAF (Fat), and PTAP (Pro).

The present disclosure further provides for, and includes, F1 progeny that are F1 hybrid animals. As used herein, an F1 hybrid animal is an animal comprising an Animal F1 Germplasm that further comprises an F1 germplasm of an animal of a different cattle breed. In an aspect, the second parent of the hybrid is a *Bos indicus* breed. In an aspect, the second parent is a member of a breed selected from the group consisting of Angus (ANG), Beef Shorthorn (SHR), Belgian Blue (BBL), Belted Galloway (BGA), Brahman (BRM), British Shorthorn (BSHN), Brown Swiss (BSW), Dutch Belted (DBE), Dutch Friesian (DFR), East Anatolian Red (EAR), English Longhorn (ELO), Finnish Ayrshire (FAY), French Brown Swiss (BRU), Galloway (GAL), Gascon (GAS), Guernsey (GNS), Hereford (HFD), Holstein (HO), Limousin (LMS), Longhorn (LHR), Milking Shorthorn (MSH), Normande (NOR), Norwegian Red (NRC), Red Angus (RGU), Texas Longhorn (TXL), Wagyu (WAG), and combinations of each.

In aspects according to the present disclosure, included are gametes obtained from F1 progeny of a first parent comprising an Animal Germplasm and a second parent having a Cheese Merit index of at least 600, a Net Merit index (NM$) of at least 600, or a Jersey Performance Index (JPI™) of at least 180. In an aspect, the second parent comprises a NM$ of at least 400. In a further aspect, the second parent comprises a NM$ of at least 500. In a further aspect, the second parent comprises a CM$ of at least 400. In a further aspect, the second parent comprises a CM$ of at least 400. Crosses of Animal to improve select DM and SM animals, results in superior F1 animals.

The present disclosure provides for, and includes, methods for improving bovine herds by selective breeding. Generally, selective breeding includes mating through natural service, artificial insemination, in vitro fertilization, and embryo transfer. As provided herein, selective breeding comprises crossing a cow of variety Animal, to a second parent, by artificially inseminating or inseminating by natural service, and calving a progeny calf. In another aspect, the disclosure provides for, and includes, providing an F1 inseminate comprising a sperm comprising an Animal Germplasm. In certain aspects, the second parent is an animal of a herd in need of improvement. In an aspect, a herd in need of improvement is a commercial herd.

In aspects according to the present disclosure, methods of improving herds further includes testing a second parent for the haplotypes JH1 and JH2 and selecting a second parent lacking one or more haplotypes JH1 or JH2.

In certain aspects, the present disclosure provides for methods of creating elite F1 Jersey progeny. In various aspects, a second Jersey parent is selected that comprises a NMS of at least 500, a CM$ of at least 500, and a JPI™ of at least 150 in any given progeny generation. In aspects of the present disclosure, the F1 progeny animals comprise a NM$ of at least 600, a CM$ of at least 600, or a JPI™ of at least 180.

The present disclosure further provides for, and includes, methods to prepare improved F1 progeny Jersey animals comprising selecting a second Jersey parent having a NM$ of at least 600, a CM$ of at least 600, or a JPI™ of at least 180. In an aspect, the second parent comprises a NM$ of at least 500. In a further aspect, the second parent comprises a NM$ of at least 400. In a further aspect, the second parent comprises a CM$ of at least 400. In a further aspect, the second parent comprises a CM$ of at least 400.

The present disclosure further provides for, and includes, Jersey F1 progeny animals, or parts thereof, comprising a NM$ of at least 600, a CM$ of at least 600, or a JPI™ of at least 180. In an aspect, the Jersey F1 progeny animals, or parts thereof, comprise a NM$ of at least 500. In a further aspect, the F1 progeny animals, or parts thereof, comprise a NM$ of at least 400. In a further aspect, the second parent comprises a CMS of at least 400. In a further aspect, the second parent comprises a CM$ of at least 400.

Also included are containers of F1 inseminates comprising a sperm comprising an F1 Animal Germplasm as recited above wherein the sperm of the inseminate is obtained from a Jersey bull having a NMS of about 400 to about 1000. In an aspect, the sperm of the inseminate is obtained from a Jersey bull having a NM$ of about 450 to about 950. In an aspect, the sperm of the inseminate is obtained from a Jersey bull having a NM$ of about 500 to about 900. In an aspect, the sperm of the inseminate is obtained from a Jersey bull having a NM$ of about 600. In various aspects, the sperm of the inseminate is obtained from a bull having a NM$ of about 500, about 550, about 600, about 650, about 700, about 750, about 800, about 850, about 900, about 950, about 1000, about 1050, or about 1100. In various aspects, the sperm of the inseminate is obtained from a bull having a CM$ of about 400 to about 900. In various aspects, the sperm of the inseminate is obtained from a bull having a CM$ of about 500 to about 800. In various aspects, the sperm of the inseminate is obtained from a bull having a CM$ of about 600 to about 700. In various aspects, the sperm of the inseminate is obtained from a bull having a CM$ of about 400, about 450, about 500, about 550, about 600, about 650, about 700, about 750, about 800, about 850, or about 900.

The present disclosure provides for, and includes, processes for storing spermatozoa comprising obtaining a *Bos taurus* ejaculate spermatozoa, each spermatozoa being a haploid cell derived from an Animal F1 offspring, mixing the *Bos taurus* ejaculate with an antibiotic to form a sperm dispersion. In an aspect, the *Bos taurus* ejaculate is an ejaculate of a bull of that is the offspring of a *Bos taurus* variety Animal. As provided herein, the sperm dispersions may further comprise one or more components selected from the group consisting of a cryoprotectant, an extender, an antibiotic, a buffer, an energy source, an antioxidant, and a protein source. In aspects of the present disclosure, the number of cells in a sperm dispersion comprise 1000 or more, $10^4$ or more, $10^5$ or more, or $10^6$ or more cells. In an aspect, the cells are in a container and comprise between $10^4$ and $10^7$ cells. In an aspect, the number of cells is between $10^5$ and $10^7$ cells.

The process for storing spermatozoa further includes preparing a straw or sheath having a volume of sperm dispersion and freezing the sperm dispersion containing straw prior to storing. In an aspect, the volume of sperm dispersion is 0.25 milliliters (ml), 0.50 ml, or any volume between 0.1 and 1 ml. As provided by the present specification, the storing comprises maintaining the sperm dispersion at a temperature of −196° C. Also included, and provided for, in the process for storing spermatozoa is sorting said spermatozoa into X-chromosome or Y-chromosome enriched inseminate. In certain aspects, the process may further comprise removing immotile spermatozoa. In aspects of the present disclosure, the number of cells in a straw, sheath or container comprises between $10^6$ to $10^8$ cells. In an aspect, the cells are in a straw, sheath or container and comprise between $10^4$ and $10^7$ cells. In an aspect, the number of cells in straw, sheath or container is between $10^5$ and $10^7$ cells. In an aspect, the concentration of spermatozoa in the sperm dispersion is between about $0.04 \times 10^6$ sperm/ml to about $12 \times 10^7$ sperm/ml.

As used herein, "transgenic animal, cell or tissue" includes reference to animals which comprises within their genomes a gene encoding a heterologous polynucleotide. Generally, the gene is stably integrated within the genome such that the expression of the polynucleotide is passed on to successive generations. The gene may be integrated into the genome alone or as part of a recombinant expression cassette. "Transgenic" is used herein to include any cell, cell line, tissue, or organ, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extrachromosomal) by conventional breeding methods or by naturally occurring events such as random cross-fertilization, non-recombinant viral infection, non-recombinant bacterial transformation, non-recombinant transposition, or spontaneous mutation. The transgene can be introduced into the genomes of the present disclosure directly or through breeding with a transgene containing animal. Methods to prepare transgenic animals are known in the art, for example by pronucleus injection as described by Gordon et al., Proc. Natl. Acad. Sci. USA 77:7380-7384 (1980). Pronucleus injection has been shown to be suitable for large domestic animals including pigs and cattle. See Hammer et al., Nature 315: 680-683 (1985) and Niemann, Proc. Natl. Acad. Sci. USA 101: 7211-7212 (2004). Other methods of generating transgenic animals are known in the art. See, such as and without limitation, Park, et al., Reprod. Fertil. Dev. 26:65-73 (2013).

Also provided for and included, are gene edited animals having an Animal Germplasm. Gene edited animals are non-transgenic animals. The animals of the present disclosure can be gene-edited animals having an Animal Germplasm or an Animal F1 Germplasm. Suitable methods for gene editing are known in the art. Methods include, but are not limited to, the methods provided in International Patent Publication No. WO 2015/148761 published Oct. 1, 2015, U.S. Pat. No. 9,868,962, published Jan. 16, 2018, and International Patent Publication No. WO 2017/132239 published Mar. 8, 2017, and references cited therein, all of which are incorporated by reference.

The gene edited animals may contain edited chromosomal sequences. The edited chromosomal sequence may be (1) inactivated, (2) modified, or (3) comprise an integrated sequence resulting in a null mutation. An inactivated chromosomal sequence is altered such that a target protein function as it relates to an undesirable phenotype is impaired, reduced or eliminated. Thus, a genetically edited animal comprising an inactivated chromosomal sequence may be termed a "knock out" or a "conditional knock out." Similarly, a genetically edited animal comprising an integrated sequence may be termed a "knock in" or a "conditional knock in." Furthermore, a genetically edited animal comprising a modified chromosomal sequence may comprise a targeted point mutation(s) or other modification such that an altered protein product is produced. Briefly, the process can comprise introducing into an embryo or cell at least one RNA molecule encoding a targeted zinc finger nuclease and, optionally, at least one accessory polynucleotide. The method further comprises incubating the embryo or cell to allow expression of the zinc finger nuclease, wherein a double-stranded break introduced into the targeted chromosomal sequence by the zinc finger nuclease is repaired by an error-prone non-homologous end-joining DNA repair process or a homology-directed DNA repair process. The method of editing chromosomal sequences encoding a protein associated with germline development using targeted zinc finger nuclease technology is rapid, precise, and highly efficient.

Alternatively, the process can comprise using a CRISPR/Cas9 system to modify the genomic sequence. To use Cas9 to modify genomic sequences, the protein can be delivered directly to a cell. Alternatively, an mRNA that encodes Cas9 can be delivered to a cell, or a gene that provides for expression of an mRNA that encodes Cas9 can be delivered to a cell. In addition, either target specific crRNA and a tracrRNA can be delivered directly to a cell or target specific gRNA(s) can be to a cell (these RNAs can alternatively be produced by a gene constructed to express these RNAs). Selection of target sites and designed of crRNA/gRNA are well known in the art.

The animal or cell can be genetically edited using a homing endonuclease. The homing endonuclease can be a naturally occurring endonuclease but is preferably a rationally designed, non-naturally occurring homing endonuclease that has a DNA recognition sequence that has been designed so that the endonuclease targets a chromosomal sequence in a target gene. Thus, the homing endonuclease can be a designed homing endonuclease. The homing endonuclease can comprise, for example, a Clustered Regularly Interspaced Short Palindromic Repeats (CRISPR)/Cas9 system, a Transcription Activator-Like Effector Nuclease (TALEN), a Zinc Finger Nuclease (ZFN), a recombinase fusion protein, a meganuclease, or a combination thereof. The animal or cell is preferably an animal or cell that has been genetically edited using a CRISPR/Cas9 system.

The following are non-limiting exemplary embodiments of the present disclosure:

1. A *Bos taurus* cell of variety Animal, a representative sample of Animal comprising the Deposit.
2. The *Bos taurus* cell according to embodiment 1, further comprising a plurality of the cell comprising a frozen vial of the plurality of the cell, a cell culture, a tissue, a zygote, an embryo, a calf, or a mature adult.
3. The *Bos taurus* cell according to embodiment 1 or 2, further comprising a plurality of the cell comprising a cow or heifer.
4. The *Bos taurus* cell according to any one of embodiments 1-3, wherein the cell is an oocyte or an ova matured therefrom.
5. The *Bos taurus* oocyte or ova according to embodiment 4, wherein the oocyte is an isolated oocyte or an isolated ova matured therefrom.
6. The *Bos taurus* oocyte according to embodiment 5, wherein the oocyte or ova is isolated for in vitro fertilization.
7. A *Bos taurus* cell produced by somatic cell nuclear transfer of a genome comprising *Bos taurus* variety Animal, a representative sample of Animal comprising the Deposit.
8. The *Bos taurus* cell according to embodiment 7, further comprising a plurality of the cell comprising a frozen vial of the plurality of the cell, a cell culture, a tissue, a zygote, an embryo, a calf, or a mature adult.
9. The *Bos taurus* cell according to embodiment 7, further comprising a plurality of the cell comprising a cow or heifer.
10. The *Bos taurus* cell according to any one of embodiments 7-9, wherein the genome of variety Animal comprises at least one edited gene.
11. The *Bos taurus* cell from an F1 offspring of an animal of variety Animal, a representative sample of Animal comprising the Deposit.
12. The *Bos taurus* cell from an F1 offspring cell according to embodiment 11, further comprising a plurality of the cell comprising meat.
13. The *Bos taurus* cell from an F1 offspring according to embodiment 11, further comprising a plurality of the cell comprising a frozen vial of the plurality of the cell, a cell culture, a tissue, a zygote, an embryo, a calf, or a mature adult.
14. The *Bos taurus* cell from an F1 offspring according to embodiment 11, further comprising a plurality of the cell comprising a bull.
15. The *Bos taurus* cell from an F1 offspring according to embodiment 11, further comprising a plurality of the cell comprising a cow or heifer.
16. The *Bos taurus* cell from an F1 offspring according to embodiment 11, wherein the offspring is conceived using in vitro fertilization.
17. The *Bos taurus* cell from an F1 offspring according to embodiment 11, wherein the offspring is conceived by artificial insemination of a superovulated cow or heifer.
18. The *Bos taurus* cell from an F1 offspring according to embodiment 17, wherein the offspring is gestated by a surrogate animal.
19. The *Bos taurus* cell from an F1 offspring according to embodiment 11, wherein the offspring is conceived by in vitro fertilization of a superovulated cow or heifer.
20. The *Bos taurus* cell from an F1 offspring according to embodiment 19, wherein the offspring is gestated by a surrogate animal.
21. The *Bos taurus* cell from an F1 offspring according to embodiment 11, wherein the F1 offspring is a gene edited animal
22. A *Bos taurus* cell from an F1 offspring according to embodiment 11, wherein the cell is a haploid cell.
23. The *Bos taurus* haploid cell from an F1 offspring according to embodiment 22, wherein the cell is a gamete.
24. The *Bos taurus* haploid cell from an F1 offspring according to embodiment 22, wherein the cell is an ovum.
25. The *Bos taurus* haploid cell from an F1 offspring according to embodiment 22, wherein the cell is a sperm.
26. The *Bos taurus* sperm according to embodiment 25, further comprising a plurality of sperm comprising semen.
27. Semen according to embodiment 26, wherein the semen is contained in a straw.
28. A straw of semen according to embodiment 27, wherein the semen is cryopreserved.
29. The *Bos taurus* cell according to any one of embodiments 20-28, wherein the haploid cell comprises at least one edited gene.

EXAMPLES

Example 1: Breeding and Selection of Animal

Animal was a progeny animal of a breeding program for the improvement of daily herds and breeding purposes. Animal had the predicted characteristics as provided above in Table 1. The definitions and abbreviations are provided above. Animal was an individual of the Jersey breed.

Animal was a cross between Sire and Dam. The composite scores and linear trait results of Sire and Dam are provided below in Table 2. Like Animal, Sire and Dam were SM and DM animals respectively, Sire is the progeny of Paternal Grand-Sire and Paternal Grand-Dam. Dam is the progeny of Maternal Grand-Sire and Maternal Grand-Dam. The composite scores and linear trait results for Animal's grandparents are provided below in Table 3.

The composite traits and other characteristics of the parents and grand-parents were determined according to methods known in the art and are presented below in Tables 2 and 3.

TABLE 2

Genomic Report for Parents of Animal

| | Sire | Dam |
|---|---|---|
| Sex | M | F |
| id17 | JE840003140305947 | JE840003136549962 |
| Birth Date | 2016 Oct. 16 | 2016 Jun. 27 |
| NM$ | 661 | 536 |
| PL | 3.1 | 3.6 |
| SCS | 2.79 | 2.90 |
| DPR | −1.8 | 0.1 |
| LIV | −0.8 | 0.2 |
| Milk | 1368 | 1198 |
| Fat | 95 | 70 |
| Pro | 62 | 47 |
| HCR | 0.2 | 0.8 |
| CCR | −1.1 | 0.7 |
| STA | −0.8 | 1.3 |
| STR | −0.3 | 0.6 |
| DFM | 0.3 | 0.6 |
| RPA | 0.1 | 0.8 |
| TRW | −0.6 | 0.2 |
| RLS | 0.1 | 0.1 |
| FTA | 0.1 | 0.0 |
| PTAT | 0.9 | 1.1 |
| FUA | 0.7 | 0.6 |
| RUH | 0.3 | 0.5 |
| RUW | 0.2 | 0.5 |
| UCL | 0.5 | 0.8 |
| UDP | 1.3 | 1.0 |
| FTP | −0.4 | 1.0 |
| TLG | 0.1 | 0.4 |
| UDC | 9.9 | 11.3 |
| CM$ | 699 | 557 |
| JPI ® | 205 | 162 |
| JH1 | T | T |
| JH2 | T | T |
| naab_code | 029JE4092 | |
| Dam | JE840003011843660 | JE840003124526579 |
| Sire | JE840003124526334 | JE840003124526245 |
| MGS | JEDNK000000302595 | JE840000067010044 |

TABLE 2

Genomic Report for Grand Parents of Animal

| | Sex | | | |
|---|---|---|---|---|
| | Paternal Grand Sire | Paternal Grand Dam | Maternal Grand Sire | Maternal Grand Dam |
| id17 | JE840003124526334 | JE840003011843660 | JE840003124526245 | JE840003124526579 |
| Birth Date | 2014 Jul. 25 | 2013 Feb. 24 | 2014 Aug.25 | 2014 Apr. 21 |
| NM$ | 574 | 755 | 514 | 573 |
| PL | 1.1 | 4.0 | 3.3 | 2.0 |
| SCS | 2.90 | 2.82 | 2.96 | 2.89 |
| DPR | −4.3 | 1.2 | 0.2 | 0.4 |
| LIV | −1.4 | −0.7 | −0.2 | 0.7 |
| Milk | 1836 | 1205 | 998 | 1284 |
| Fat | 90 | 107 | 68 | 85 |
| Pro | 71 | 59 | 46 | 44 |
| HCR | −2.7 | 2.8 | 0.3 | 0.1 |
| CCR | −3.5 | 1.7 | 1.1 | −0.2 |
| STA | 0.9 | −0.4 | 1.1 | 0.2 |
| STR | 0.7 | 0.2 | 0.7 | 0.1 |
| DFM | 1.0 | 0.5 | 0.6 | 0.5 |
| RPA | 0.7 | −0.6 | −0.1 | 0.5 |
| TRW | 0.1 | 0.1 | 0.6 | −0.4 |
| RLS | 0.1 | 0.2 | −0.4 | 0.3 |
| FTA | 0.1 | 0.5 | 0.1 | 0.2 |
| PTAT | 1.4 | 0.8 | 1.0 | 0.9 |
| FUA | 0.8 | 0.3 | 0.7 | 0.8 |
| RUH | 1.0 | 0.1 | 0.6 | 0.9 |
| RUW | 0.7 | 0.4 | 0.5 | 0.4 |
| UCL | 0.4 | 0.5 | 0.3 | 0.3 |
| UDP | 0.8 | 0.8 | 0.9 | 0.8 |
| FTP | 0.1 | −0.7 | 0.5 | 0.5 |
| TLG | 0.7 | 0.6 | 1.1 | 0.5 |
| UDC | 9.1 | 4.9 | 7.7 | 9.2 |
| CM$ | 602 | 796 | 541 | 584 |
| JPI ® | 172 | 227 | 152 | 166 |
| JH1 | T | T | T | T |
| JH2 | T | T | T | T |
| Naab_code | 001JE0921 | | 007JE01477 | |
| Dam | JE840003011216168 | JE840003001860402 | JE840003005623248 | JE840003007109191 |
| Sire | JE840000118157731 | JEDNK000000302595 | JE840000118201001 | JE840000067010044 |
| MGS | JE840000117422971 | JE840000111023978 | JE840000111947650 | JE840000115468148 |

Example 2: Culture of *Bos taurus* Cells

Adult *Bos taurus* fibroblast cultures are established from ear punch or tail clip from Animal at an age of less than one year according to standard methods.

Briefly, an ear punch or tail clip is treated with collagenase and digested. The collagenase treated cells are then collected by centrifugation and washed with buffered saline.

The washed cells are treated with trypsin and triturated and a suspension of cells plated on standard culture dishes and cultured under standard conditions to prepare a primary culture. The cells are cultured and either fed or split 1:4 to 1:6 and the culture expanded. Cells are harvested when the culture reaches at least 10 million. At confluence, cells are collected by trypsin/EDTA treatment and centrifugation. Cells are resuspended and counted and then collected and resuspended a concentration of $1\times10^6$-$10^7$/mL. Cells are diluted with freezing medium (90% FBS+10% DMSO). Tubes are transferred to $-80°$ C. overnight before being placed in liquid nitrogen for long term storage. Cells prepared by this method are deposited under ATCC Accession No. PTA-126146.

Example 3: Somatic Cell Nuclear Transfer (Scnt) of Animal Cells

Somatic cell nuclear transfer (SCNT) is performed according the method of Ross and Cibelli, *Methods Mol Biol*. 636. 155-77 (2010). See also U.S. Pat. No. 6,011,197 issued Jan. 4, 2000, to Strelchenko et al.

Briefly, five to seven days before performing SCNT, a culture of fibroblasts as described in Example 3 are plated in four well dishes at a density of 100,000 cells per well and cultured. The cells are synchronized in the G0 stage by contact inhibition. Oocytes are harvested from either slaughterhouse-derived ovaries or from live animals by ultrasound-guided oocyte aspiration. The oocytes are matured in vitro and enucleated. The cultured fibroblasts are injected into enucleated oocytes and oocyte-cell fusion is induced using a square DC pulse generator. Fused oocytes are activated using ionomycin and cultured under standard conditions. At 48 h after activation, noncleaved embryos are removed from culture and at 72 h after activation, the culture medium is supplemented with serum and cultured for seven days before being recovered and implanted in synchronized recipients. Calves are born normally to the surrogate mother and are genetically identical offspring to Animal. In addition to providing a source of transferred embryos for herd improvement, new cultures of cells as described in Example 2 can be prepared. The high availability of bovine oocytes and the relatively higher efficiency levels usually obtained in cattle provide for the use of SCNT for both commercial and research purposes.

Example 4: Breeding of Animal Progeny

Mature F1 bulls prepared by the methods of the present specification are used for breeding purposes using conventional artificial insemination methods. Alternatively, bulls prepared by SCNT can be used for natural service.

Frozen inseminate obtained as provided below in Example 5 is provided for artificial insemination for the improvement of existing herds. Breeding for the improvement of existing herds does not generally require consideration of the recipient heifer or cow. In an aspect, a dam is selected from a herd in need of improvement and artificially inseminated with Animal F1 inseminate. In an aspect, a herd in need of improvement has an average NM$ index of less than 400. In an aspect, a herd in need of improvement has an average NM$ index of between 400 and 600. After gestation, calves are born and evaluated for production, composite traits, and predicted transmitting abilities. In some cases, genomic testing is performed. The resulting calves have improved NM$ and other desirable traits as compared to the parent dam and as compared to other calves born in the herd.

The frozen inseminate obtained as provided below in Example 5 is also used for the generation of elite bulls and heifers. Frozen inseminate obtained as provided below in Example 5 is provided for artificial insemination to an elite DM animal having an NM$ index of at least 500. After gestation, the calf is genotyped and identified for predicted characteristics, composite traits, and predicted transmitting abilities. A calf having improved traits is selected and used for further breeding and for the improvement of existing herds.

Example 5: Progeny Generation Using In Vitro Fertilization and Embryo Transfer

Semen from mature Animal F1 bulls is collected by electroejaculation or by other methods known in the art: The collected semen is frozen in straws per methods known in the art. Progeny are generated by thawing a straw of frozen semen and the thawed semen used for artificial insemination. In short, about 5 ml to about 15 ml of semen is collected from a bull after being electroejaculated and mixed with a suitable extender and cryoprotectant. About 10 ml of semen is collected and mixed with about 240 ml of TRILADYL™ solution (Minitube of America, Verona, Wis.) The mixture of semen, extender and cryoprotectant is then placed in plastic straws. Straws containing about 20 million motile sperm in a volume of about ½ ml are obtained and frozen until needed. Prior to use, frozen straws are thawed.

The collected semen of the present specification may be frozen according to standard methods in the art as discussed above.

Example 6: Generation of Multiple Embryos by Superovulation and In Vitro Fertilization An Animal cow or heifer is treated with follicle stimulating hormone to induce multiple ovulations. Following superovulation, Animal is bred using artificial insemination of an elite inseminate. About seven days after insemination, embryos are non-surgically collected by 'flushing' from the donor's uterus and transferred into synchronous recipients that serve as surrogate mothers. Embryos may be frozen for implantation at a later date.

Embryos are also generated using IVF collection of unfertilized oocytes from the ovaries of a donor cow or heifer. Oocytes are fertilized in vitro and transferred seven days after fertilization following incubation under controlled conditions. IVF collection and fertilization allows for the generation of multiple embryos obtained from an Animal cow or heifer.

Embryos are transferred to a surrogate and gestated until birth.

Example 7: Generation of Multiple Embryos by Superovulation and In Vitro Fertilization The Animal F1 inseminate collected as provided in Example 5 is used for in vitro fertilization of oocytes collected from a heifer or cow to create multiple embryos. The heifer or cow is treated with follicle stimulating hormone to induce multiple ovulations. Following superovulation, the donor heifer or cow is bred using artificial insemination of the Animal F1 inseminate. About seven days after insemination, embryos are non-surgically collected by 'flushing' from the donor's uterus and transferred into synchronous recipients that serve as surrogate mothers. Embryos may be frozen for implantation at a later date.

Embryos are also generated using IVF collection of unfertilized oocytes from the ovaries of a donor cow or heifer. Oocytes are fertilized in vitro and transferred seven days after fertilization following incubation under controlled conditions. IVF collection and fertilization allows for the generation of multiple embryos obtained from open cows, pregnant cows, heifers and females having difficulty in conventional breeding. IVF collection also provides for collection of oocytes from donors shortly after death. Embryos are transferred to a surrogate and gestated until birth.

All publications are herein incorporated by reference, each in their entirety.

What is claimed is:

1. A *Bos taurus* cell comprising JE840003146074527 germplasm, a representative sample of JE840003146074527 germplasm having been deposited under ATCC accession number PTA-126146.

2. A frozen vial, a cell culture, a tissue, a zygote, or an embryo comprising a plurality of the *Bos taurus* cell according to claim 1.

3. A cow or heifer comprising a plurality of the *Bos taurus* cell according to claim 1.

4. The *Bos taurus* cell according to claim 1, wherein the cell is an oocyte or an ova matured therefrom.

5. The *Bos taurus* oocyte or ova according to claim 4, wherein the oocyte or an ova matured therefrom is an isolated oocyte or an ova matured therefrom.

6. The *Bos taurus* oocyte or ova according to claim 5, wherein the oocyte or an ova matured therefrom is isolated for in vitro fertilization.

7. A *Bos taurus* cell produced by somatic cell nuclear transfer of JE840003146074527 germplasm, a representative sample of JE840003146074527 germplasm having been deposited under ATCC accession number PTA-126146.

8. A frozen vial, a cell culture, a tissue, a zygote, or an embryo comprising a plurality of the *Bos taurus* cell according to claim 7.

9. A cow or heifer comprising a plurality of the *Bos taurus* cell according to claim 7.

10. The *Bos taurus* cell according to claim 7, wherein the genome comprises at least one edited gene.

11. A *Bos taurus* cell from an F1 offspring of a *Bos taurus* animal comprising JE840003146074527 germplasm, a representative sample of JE840003146074527 germplasm having been deposited under ATCC accession number PTA-126146.

12. Meat comprising a plurality of the *Bos taurus* cell from an F1 offspring cell according to claim 11.

13. A frozen vial, a cell culture, a tissue, or a zygote comprising a plurality of the *Bos taurus* cell according to claim 11.

14. A bull comprising the *Bos taurus* cell from an F1 offspring according to claim 11.

15. A cow or heifer comprising the *Bos taurus* cell from an F1 offspring according to claim 11.

16. The *Bos taurus* cell from an F1 offspring according to claim 11, wherein the offspring is conceived using in vitro fertilization.

17. The *Bos taurus* cell from an F1 offspring according to claim 11, wherein the offspring is conceived by artificial insemination of a superovulated cow or heifer.

18. The *Bos taurus* cell from an F1 offspring according to claim 17, wherein the offspring is gestated by a *Bos taurus* surrogate mother.

19. The *Bos taurus* cell from an F1 offspring according to claim 11, wherein the offspring is conceived by in vitro fertilization of an ovum obtained from a superovulated cow or heifer.

20. The *Bos taurus* cell from an F1 offspring according to claim 19, wherein the offspring is gestated by a *Bos taurus* surrogate mother.

21. The *Bos taurus* cell from an F1 offspring according to claim 11, wherein the F1 offspring is a gene edited *Bos taurus* animal.

22. A *Bos taurus* cell from an F1 offspring according to claim 11, wherein the cell is a haploid cell.

23. The *Bos taurus* haploid cell from an F1 offspring according to claim 22, wherein the cell is a gamete.

24. The *Bos taurus* haploid cell from an F1 offspring according to claim 22, wherein the cell is an ovum.

25. The *Bos taurus* haploid cell from an F1 offspring according to claim 22, wherein the cell is a sperm.

26. Semen comprising a plurality of the *Bos taurus* sperm according to claim 25.

27. Semen according to claim 26, wherein the semen is contained in a straw.

28. Semen according to claim 27, wherein the semen is cryopreserved.

29. The *Bos taurus* cell according to claim 22, wherein the haploid cell comprises at least one edited gene.

30. A container of semen produced by the bull of claim 14.

* * * * *

Disclaimer

10,975,351 B2 - Aaron Horst, Chambersburg, PA (US); Katrina Dattilo, Waunakee, WI (US); Devan Funk, DeFrost, WI (US). Patent dated April 13, 2021. Disclaimer filed May 26, 2022, by the assignee, ABS Global, Inc.

I hereby disclaim the following complete claims 1-30 of said patent.

*(Official Gazette, October 25, 2022)*